(12) United States Patent
Metz

(10) Patent No.: US 11,517,375 B2
(45) Date of Patent: Dec. 6, 2022

(54) BONE CEMENT AUGMENTATION PROCEDURE

(71) Applicant: MAZOR ROBOTICS LTD., Caesarea (IL)

(72) Inventor: Ben Metz, Tel Aviv (IL)

(73) Assignee: MAZOR ROBOTICS LTD., Caesarea (IL)

( * ) Notice: Subject to any disclaimer, the term of this patent is extended or adjusted under 35 U.S.C. 154(b) by 870 days.

(21) Appl. No.: 16/348,151

(22) PCT Filed: Nov. 8, 2017

(86) PCT No.: PCT/IL2017/051219
§ 371 (c)(1),
(2) Date: May 8, 2019

(87) PCT Pub. No.: WO2018/087758
PCT Pub. Date: May 17, 2018

(65) Prior Publication Data
US 2019/0254750 A1    Aug. 22, 2019

Related U.S. Application Data

(60) Provisional application No. 62/418,813, filed on Nov. 8, 2016.

(51) Int. Cl.
*A61B 34/10*      (2016.01)
*A61B 17/88*      (2006.01)
(Continued)

(52) U.S. Cl.
CPC .............. *A61B 34/10* (2016.02); *A61B 6/032* (2013.01); *A61B 6/505* (2013.01);
(Continued)

(58) Field of Classification Search
None
See application file for complete search history.

(56) References Cited

U.S. PATENT DOCUMENTS

| 2004/0009459 A1 | 1/2004 | Anderson |
| 2007/0219455 A1 | 9/2007 | Wong et al. |

OTHER PUBLICATIONS

Zheng et al. (Vertebral Augmentation With a Novel Vessel-X Bone Void Filling Container System and Bioactive Bone Cement, Spine, vol. 32, No. 19, 2007) (Year: 2007).*

(Continued)

*Primary Examiner* — Kyle Zhai
(74) *Attorney, Agent, or Firm* — Sheridan Ross P.C.

(57) ABSTRACT

A method for planning the insertion of bone cement into an orthopedic void of a vertebra. A three dimensional preoperative image of the vertebra is used and the voxels are analyzed to provide the voxel absorption levels. The absorption levels are transformed into mechanical properties of regions of the vertebra, such that a three dimensional mesh of the mechanical properties of the vertebra is generated. An entry point and an entry angle are selected on the vertebra, through which to inject bone cement into the void. Then, using the known viscosity of the bone cement, and using the entry point and entry angle, a finite elements analysis may be performed on the mesh to simulate the propagation of the (Continued)

bone cement into the orthopedic void. The simulation is repeated using different operational parameters until said propagation of said bone cement is deemed satisfactory.

21 Claims, 6 Drawing Sheets

(51) Int. Cl.
| | | |
|---|---|---|
| *G16H 20/40* | (2018.01) | |
| *G16H 50/50* | (2018.01) | |
| *G16H 30/40* | (2018.01) | |
| *A61B 6/03* | (2006.01) | |
| *A61B 6/00* | (2006.01) | |
| *G06T 17/20* | (2006.01) | |

(52) U.S. Cl.
CPC .......... *A61B 17/8805* (2013.01); *G06T 17/20* (2013.01); *G16H 20/40* (2018.01); *G16H 30/40* (2018.01); *G16H 50/50* (2018.01); *A61B 17/8855* (2013.01); *A61B 2017/8844* (2013.01); *A61B 2034/104* (2016.02); *A61B 2034/105* (2016.02); *A61B 2034/107* (2016.02); *G06T 2210/41* (2013.01)

(56) References Cited

OTHER PUBLICATIONS

Jones et al. (Finite element analysis of the spine: Towards a framework of verification, validation and sensitivity analysis, Medical Engineering & Physics 30 (2008)) (Year: 2008).*

D. W. Overaker, N. A. Langrana and A. M. Cuitiño. Finite Element Analysis of Vertebral Body Mechanics With a Nonlinear Microstructural Model for the Trabecular Core, J Biomech Eng 121(5), 542-550 (Oct. 1, 1999) doi:10.1115/1.2835085.

International Search Report and written opinion of the ISA for PCT/IL2017/051219, dated Feb. 8, 2018 (already uploaded by USPTO).

Badilatti et al., Journal of Orthopaedic Translation (2015), pp. 185-196, Oct. 1, 2015.

Landgraf et al., ZAMM—Journal of Applied Mathematics and Mechanics, vol. 95 No. 12, pp. 1530-1547, Dec. 2015.

* cited by examiner

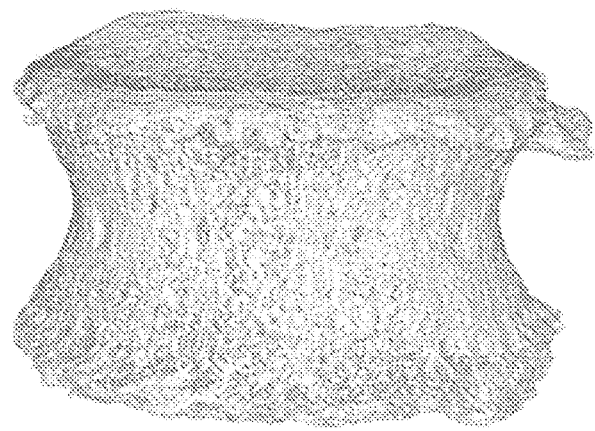
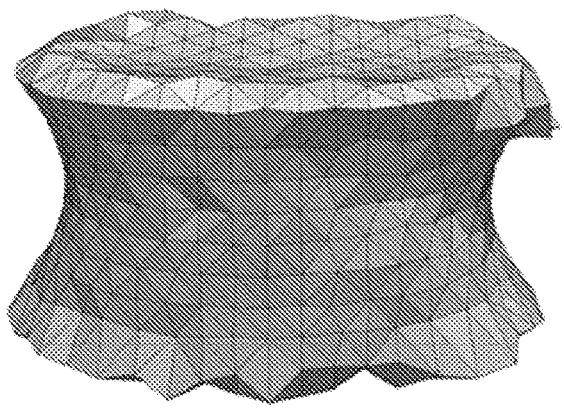
FIG. 6A　　　　　　　FIG. 6B
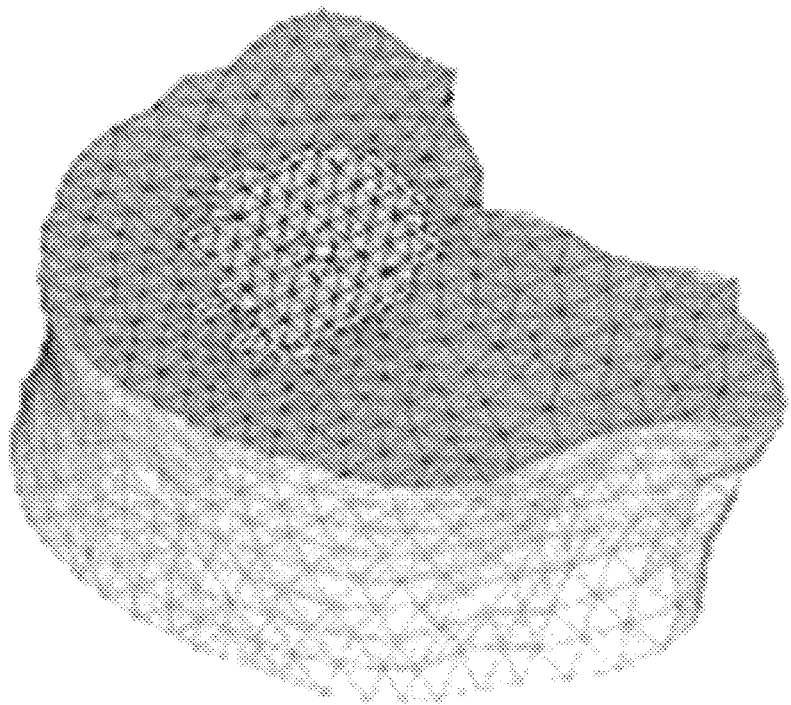
FIG. 7

BONE CEMENT AUGMENTATION PROCEDURE

FIELD OF THE INVENTION

The present invention relates to the field of the augmentation of orthopedic structures by the injection of bone cement into bones, especially as applied to the support of vertebral body structures.

BACKGROUND

In patients with osteoporosis or other diseases involving structural bone weakness, a vertebral condition known as compression fracture, or a fracture in the form of a cleft fracture can occur. Alternatively, the complete vertebral body can distort such that the end plates of the body of a vertebra are not aligned vertically opposite each other. Surgical orthopedic bone cement augmentation procedures, known as Kyphoplasty or Vertebroplasty, are procedures for treating such collapsed, distorted or fractured vertebral bodies. They are implemented by injecting into the vertebral body, bone-cement for fortification and augmentation thereof by increasing the distance between the vertebral end-plates. Polymethyl methacrylate or PMMA is commonly used as the bone-cement. The procedure is intended to alleviate pressure on the nerve roots and restore stability to the bony anatomy through decreased mobility. By doing so, significant reduction of pain, and the restoration of sensation and the ability to perform daily functions are expected to be accomplished.

Kyphoplasty, as opposed to Vertebroplasty, includes the additional step of inflating at high pressure (typically up to 100 psi) a balloon inserted into the vertebral body, to create a void within the cancellous bone, before introducing the bone-cement. This additional step has two main objectives:
(i) To ensure that there is sufficient volume into which the bone-cement is injected and hence to decrease the chances of it leaking out.
(ii) To obtain an estimation on the augmentation potential of the vertebral body.

However, any of the above mentioned pathological conditions can result in cracks in the vertebral shell, such that as the cement is injected into the body, it can leak out of any such cracks or clefts, causing collateral damage to anatomical features around the vertebral body. Especially critical is leakage from the back wall of the vertebral body, in the region where the blood vessels enter the vertebral body, and where any leakage could cause rupture of blood vessels resulting in hemorrhaging, or conversely, starvation of the bone tissue because of lack of blood flow. Additionally, excess bone cement may also leak into the spinal canal with possible serious neurological damage to the spinal cord. Therefore, it is important to know the volume of cement which is required to fill the voids and to just generate the support required, and hence to stop injection of the cement before any quantity has leaked out of the vertebra.

Therefore, the objective of either type of surgery is typically to deliver as much bone-cement as possible into the vertebral body, without causing a spill-over, which is known as cement extravasation. The amount of cement inserted must be carefully estimated in order to ensure the success of the treatment. The consequences of undersupplying bone-cement may be ineffective treatment. On the other hand, the consequences of a spill-over may be merely ineffective treatment if the bone-cement only leaks laterally, but more seriously, neurological damage if the bone-cement leaks postero-medially into the spinal canal or posteriorly into the neural foramen.

Therefore, to prevent both undersupplying and spill-over of bone-cement, the surgery is performed under fluoroscopy with x-ray images being acquired after every small insertion step in order to closely monitor the progress. Typically, the surgeon will request lateral C-arm images with every small step or action performed, followed by final AP images to check the cement position after the procedure. This procedure entails 30-60 seconds of fluoroscopy, exposing the attending staff and the patient to a significant amount of radiation. Additionally, while being an effective tool for preventing harm to the patient, the use of fluoroscopy does not generally ensure the optimal treatment, since there is presently no way using fluoroscopy to precisely estimate the optimal injection point, the spatial direction and the optimal amount of injected bone-cement.

There therefore exists a need for an improved method for implementing bone cement augmentation, which overcomes at least some of the disadvantages of prior art systems and methods.

The disclosures of each of the publications mentioned in this section and in other sections of the specification, are hereby incorporated by reference, each in its entirety.

SUMMARY

The present disclosure describes new exemplary methods for determining parameters for cement augmentation surgery using software simulation to improve the accuracy of the procedure. The method uses a finite element analysis, based on medical imaging of a patient's bony anatomy from an appropriate modality, such as CT, MRI or Ultrasound. Parameters determined from this method include primarily an estimate of the correct amount of bone cement to use, and in addition, the positioning and direction of the cement-delivery system in order to obtain optimum fill of the vertebral void without potentially dangerous spill-over.

An additional step in this method may be the provision of instructions to a robotic guidance system, to physically guide placement and orientation of the cement-delivery system, using the modeling parameters.

Insertion of the cement generally using a biopsy or Jamshidi needle, has to be performed speedily since the viscosity of the cement increases with time as the cement undergoes curing to its hardened state. Therefore, it is important that the surgeon knows in advance what volume of cement is to be injected into the bone, to determine if sufficient cement will be injected or not. The methods of the present application provide the surgeon with information about the optimal quantity of cement to inject, such that it will efficiently fill all of the void space available, yet without any excess cement leaking out. The method also provides the surgeon with the information to enable injection of the cement according to a predetermined trajectory into the voids observed in the images obtained from a preoperative CT. In addition, the methods of the present disclosure enable the use of robotic insertion of the injection needle, such that it can be positioned at the orientation and with the tip at the exact position which will optimally insert the cement to fill the void. The method enables the procedure to be performed minimally invasively, and more importantly, with significantly lower X-radiation exposure than with the prior art methods of using fluoroscopy-guided insertion to follow the course of the cement deployment in the vertebra.

The methods of this disclosure and the system for implementing those methods, are based on a determination of the structural make-up of the voids within the vertebral body, and a finite elements analysis of this vertebral structure, both its spatial structure and its mechanical strength, using the mechanical characteristics of the cement and the void structure, in order to determine the flow dynamics of the infusion of the cement through the void, and the correct quantity of cement to fill the voids, and the optimum position and angle of the injection needle to achieve that aim. The methods are based on the transformation of the grey level of the preoperative CT images, expressed in Hounsfield Units, into the mechanical characteristics of the bone structure, and translating that information into a mesh which represents the imaged bone structure, including its voids, their spatial boundaries, extent and bone porosities, and the associated mechanical strength of the various elements of the mesh, and the shape, extent and porosity of any passageways or niches within the void or branching off therefrom. The void structure is defined by taking a CT image and generating therefrom a three dimensional mesh of finite elements, element of the mesh being defined by the grey level of the CT image voxel or group of voxels corresponding to that element. The grey level is representative of the density of the bone in that voxel, and each voxel may then be attributed mechanical properties based on the x-ray attenuation of the equivalent CT voxel. The elements of the mesh can then be used for a finite element analysis of the region of interest. The viscosity of the cement is input into the program, and characteristic forces are applied thereto within the mesh representation. Then, by using fluid dynamics equations operating on the cement within a mesh having those ascertained mechanical characteristics, the finite elements program can determine how the injected cement behaves within the bone void in accordance with the mechanical characteristics of each voxel of the void, and the shape and size of the void. Since the cement is injected into the bone structure at a high pressure, typically of up to 100 psi, the flow will, depending on the mechanical strength of the bone in each region of the mesh, cause parts of the bone structure to be either compressed or distorted, or even to be swept away completely by the cement flow, thereby also changing the void geometry of the vertebral body.

The software is able to utilize a series of frames of the CT image set, each representing a two-dimensional view of a particular plane of a vertebral body, and, using a set of predetermined rules for conversion of grey levels to mechanical characteristics of the bone, to generate therefrom a three-dimensional mesh for use in the finite elements program. The lateral and AP structure is obtained from the axial views of the vertebra, and the third dimensional information about the vertebra structure is obtained by using a series of frames of the CT image set, at spaced apart axial levels of the vertebra.

The following data can be extracted from the series of CT image frames:
(a) the three dimensional shape of a void in the vertebral body;
(b) the three dimensional form of the passageways and niches associated with that shape; and
(c) the bone density, from which porosity and the mechanical strength of the bone can be determined at every point throughout the imaged bone.

From this data, a mesh can be generated on which the finite elements analysis can be applied. This data also enables the maximum allowed total volume of cement required for the procedure to be calculated. The surgeon can then decide, either by his own experience from viewing the CT images themselves, or by an inspection of the generated mesh, where an advantageous point at which to inject the cement is located, and at what angle. Once the data is input into the program to generate the mesh, together with the known viscosity of the cement and the pressure at which it is introduced, the finite element routine can then calculate the expected flow of cement injected at the determined position and angle through the various hollows and passages of the vertebral body void, including any structural changes generated by the injection of the cement itself, until the maximum calculated volume of cement has been deployed. The surgeon can view the result of the simulation to ascertain whether the cement spread is expected to fulfil the clinical requirements of the procedure. Should the simulation show that the estimation of the cement volume was erroneous, and that the cement fills the entire void and begins to seep out through cracks or orifices in the vertebral body, the quantity of cement can be reduced accordingly. Should the simulation show that the estimation of the cement volume was erroneous, and that the cement does not sufficiently fill the void, the quantity of cement can be increased accordingly. Should the flow characteristics provide the result that not all of the cement can deploy within the time allowed before the viscosity of the cement becomes such as to prevent further significant flow, a cement composition having a reduced viscosity or a slower curing speed can be used, or a higher insertion pressure used, commensurate with safety of the bone structure. According to a further aspect of the finite element algorithm, the rate of deployment and infiltration of the cement can be time-related to the increase in viscosity expected with the passage of time during the injection, to provide a more accurate simulation of the cement entry.

Complete use of the finite element program enables a simulation to be generated for the entry of the cement into the vertebral void structure. Once the surgeon has made an initial selection of the entry point and angle of the delivery device, and the delivery point of the cement, the finite elements routine is run, and a simulation of the extent of deployment of the cement is obtained. If this simulation indicates that the extent or the uniformity of deployment of the cement is insufficient, (i.e. the deployment of the cement into each crack, cleft or part of the void), or more importantly, that the extent of deployment of the cement is excessive, causing cement leakage, then, based on the results obtained from the simulation, the surgeon can do any of:
(i) adjust the quantity of cement injected, and
(ii) select at least one of an alternative entry point and angle, so that a better coverage of cement should be obtained,
(iii) adjust the cement composition, changing its viscosity, and
(iv) adjust the cement insertion pressure.

The simulation can then be run again to ascertain whether a better result is obtained. Such simulations can be run iteratively until an optimum filling of cement is obtained. Once the optimum simulation has been obtained, the program can output directly to the robotic control system, instructions to align the robot such that the exact placement and angle of the needle for that particular iteration, is obtained.

The use of this procedure enables the amount of X-radiation required during the cement augmentation operation to be reduced dramatically.

The above described summary describes the factors involved for a vertebroplasty procedure. For the performance of kyphoplasty, the mechanical strength parameters of the bone elements of the mesh acquire a more important status, since it is those parameters, such as the Young's modulus, and the strain rate of the bone of the element, that determine how much, and in which directions, the inflation balloon will compress, translate and distort the weak cancellous bone structure within the vertebral body to form the desired void, even before the application of the cement insertion steps. Thus, for kyphoplasty procedures, the optimum simulation will involve a two part FEA, with the first part simulating the balloon inflation and how it changes the structure and estimated mechanical characteristics of the vertebral body, both for the void being created by the balloon inflation, and in the regions of the vertebral body beyond the void created by the inflation balloon, and the second part simulating the cement introduction into the newly generated internal structure of the vertebral body. A more accurate procedure could use an imaging step between these two procedures, in order to determine more accurately how the balloon inflation and it concomitant pressure on the bone structure has actually changed the surrounding structure, but since the balloon inflation and the cement introduction is most advantageously performed in one operating room procedure, this intermediate imaging step is not generally practical or even required for the level of accuracy needed for the cement augmentation.

Due to the large number of adjustable parameters in the disclosed methods, the cumulative effect of which determines the outcome of the procedure, it may be advantageous to use a computerized routine to determine how to adjust the parameters of the procedure in order to obtain a successful outcome. The computer routine may use an image processing program in order to assess the success of the simulation performed, and on the basis of a database of previously performed simulations, having known correlations between these parameters and their outcomes, may suggest which parameters to adjust and by how much in order to obtain a more acceptable result. Such a database may be derived from a large number of anatomical images and cement flow simulations derived from these images. Furthermore, such a computerized routine may use machine learning or artificial intelligence to increase the success rate of its suggested outcomes. Such a computerized routine may also be used for kyphoplasty procedures in order to determine optimal balloon inflation parameters.

The adjusted parameters described above may thus be determined either by a medical professional or by a computerized routine, or by collaboration between both. For example, the computer may use suggested parameters to produce simulations for the surgeon to review. The computerized routine may suggest any of a different quantity of cement injected, an alternative entry point or angle, a different cement composition, a different cement viscosity, and a different the cement insertion pressure, or it may suggest a range relating to any of these parameters.

Finally, although the procedures described in this disclosure have used the insertion of bone cement into a vertebral body as the example to illustrate the method, it is to be understood that the same procedures may also be used in other orthopedic situations where bone cement insertion is required, in circumstances where the correct propagation and fill of the cement is important, such as in femoral joint reconstruction, and in knee joint reconstruction. The methods of this disclosure are not thus intended to be limited to cement augmentation of vertebral bodies.

There is thus provided in accordance with an exemplary implementation of the methods described in this disclosure, a method of planning the insertion of bone cement into an orthopedic void of a vertebra, the method comprising:

(a) providing a three dimensional preoperative image comprising at least the vertebra, (b) generating from the three dimensional preoperative image, a three dimensional mesh of finite elements, (c) using a predetermined conversion criterion, transforming the image absorption levels of the voxels to a mechanical property of corresponding voxels of the vertebra, and attributing to elements of the mesh, the mechanical property of the corresponding voxels of the vertebra, such that a three dimensional mesh of the mechanical property of the region of the vertebra is generated, (d) selecting an entry point and an entry angle on the vertebra, through which to inject the bone cement into the void, (e) using the known viscosity of the bone cement, and using the entry point and entry angle, performing a finite elements analysis on the three dimensional mesh of the selected mechanical property to simulate the propagation of the bone cement into the orthopedic void, and (f) if the propagation is deemed unsatisfactory, repeating the simulation using at least one of a different quantity of bone cement, a cement of different viscosity, a different entry point, a different entry angle, a different cement delivery point, and a different cement insertion pressure.

In this method, the mechanical property may be at least one of (i) bone porosity, (ii) bone density, (iii) Young's modulus, (iv) strain rate, (v) shear rate, and (vi) compressive strength.

In such a method, the repeating may be performed iteratively until the propagation of the bone cement is deemed satisfactory.

According to further implementations of these methods, the propagation of the bone cement may be deemed unsatisfactory if either (i) the bone cement is shown to leak out of the vertebra, (ii) the bone cement does not sufficiently fill the orthopedic void, and (iii) the bone cement does not deploy throughout the orthopedic void before the increased viscosity of the bone cement prevents its required further flow.

The method may further comprise the step of using the determined entry point and entry angle to provide information for input to a robotic guidance system for alignment of an injection device.

Additionally, in these methods, any of the simulations may take into consideration the increase in viscosity of the bone cement that is expected with the passage of time.

Furthermore, the three dimensional preoperative image may be generated from a set of two dimensional images. In any of these cases, the three dimensional preoperative image may be a CT scan. If so, the absorption level is then the x-ray attenuation level.

According to yet another implementation of the above described methods, the at least one of a different quantity of bone cement, a different entry point, a different entry angle, a different insertion pressure, a different cement delivery point and a cement of different viscosity, may be determined by either or both of a medical professional or a computerized program.

Still other example implementations involve an alternative method of planning the insertion of bone cement into an orthopedic void of a vertebra, the method comprising:

(a) providing a three dimensional preoperative image comprising at least the vertebra, (b) generating from the three dimensional preoperative image, a three dimensional mesh of finite elements, (c) using a predetermined conversion criterion, transforming the image absorption levels of the voxels to a mechanical property of corresponding voxels of the vertebra, and attributing to elements of the mesh, the mechanical property of the corresponding voxels of the vertebra, such that a three dimensional mesh of the mechanical property of the region of the vertebra is generated, (d) selecting an entry point and an entry angle on the vertebra, through which to insert an inflation balloon into the vertebrae to generate an enlarged void, and through which to inject the bone cement into the void, (e) using the generated three dimensional mesh of the mechanical property of the vertebra, performing a finite elements analysis to determine the shape and extent of the enlarged void generated by inflation of the balloon, (f) using the known viscosity of the bone cement, and using the shape and extent of the enlarged void, performing a finite elements analysis on the three-dimensional mesh of the mechanical property to simulate the propagation of bone cement injected into the enlarged void, and (g) if the propagation is deemed unsatisfactory, repeating the simulation using at least one of a different balloon inflation condition, a different quantity of bone cement, a cement of different viscosity, a different entry point, a different entry angle, a different insertion pressure, and a different cement delivery point.

In this alternative method, the mechanical property may be at least one of (i) bone porosity, (ii) bone density, (iii) Young's modulus, (iv) strain rate, (v) shear rate, and (vi) compressive strength.

In such an alternative method, the repeating may be performed iteratively until the propagation of the bone cement is deemed satisfactory.

According to further implementations of these alternative methods, the propagation of the bone cement may be deemed unsatisfactory if either (i) the bone cement is shown to leak out of the vertebra, (ii) the bone cement does not sufficiently fill the orthopedic void, and (iii) the bone cement does not deploy throughout the orthopedic void before the increased viscosity of the bone cement prevents its required further flow.

The alternative methods may further comprise the step of using the determined entry point and entry angle to provide information for input to a robotic guidance system for alignment of an injection device.

Additionally, in these alternative methods, any of the simulations may take into consideration the increase in viscosity of the bone cement that is expected with the passage of time. Furthermore, the three dimensional preoperative image may be generated from a set of two dimensional images. In any of these cases, the three dimensional preoperative image may be a CT scan. If so, the absorption level is then the x-ray attenuation level.

Finally, according to yet another implementation of the above described alternative methods, the at least one of a different balloon inflation condition, a different quantity of bone cement, a different entry point, a different entry angle, a different insertion pressure, a different cement delivery point and a cement of different viscosity, may be determined by either or both of a medical professional or a computerized program.

BRIEF DESCRIPTION OF THE DRAWINGS

The present invention will be understood and appreciated more fully from the following detailed description, taken in conjunction with the drawings in which:

FIGS. 6A and 6B illustrate the generation of a finite elements mesh of the vertebral body;

FIG. 7 illustrates a finite elements mesh of a vertebra body, after a simulation of the injection of bone cement, the simulation being performed by means of a finite elements analysis;

DETAILED DESCRIPTION

Figure 1A:
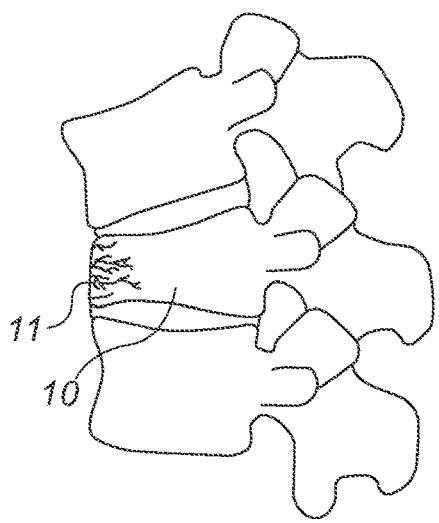
FIGS. 1A and 1B illustrate schematically the performance of a vertebroplasty procedure performed on a vertebral body.
Figure 1B:
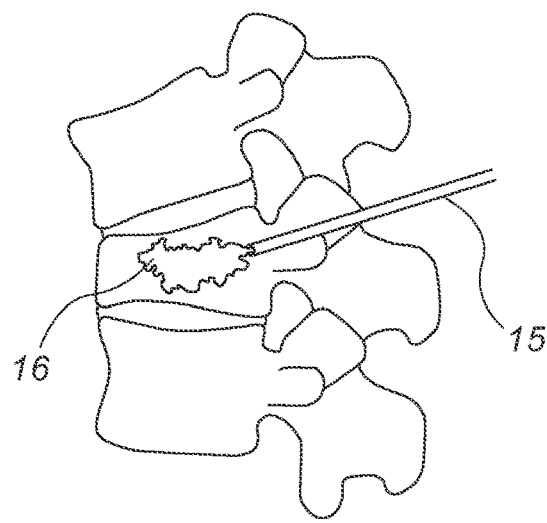

Reference is first made to FIGS. 1A and 1B, which illustrate schematically the performance of a vertebroplasty procedure performed on a vertebral body. In FIG. 1A, it is observed that the vertebral body 10, has a compression fracture 11, possibly caused by osteoporosis. In FIG. 1B, there is shown an insertion device 15, such as a biopsy needle or a Jamshidi needle, inserted through the pedicle region of the vertebra, and the deployment of bone cement 16 to fill voids in the vertebral body, and hence to support the vertebral body from further collapse from the spread of the fracture cracks.

Figure 2A:
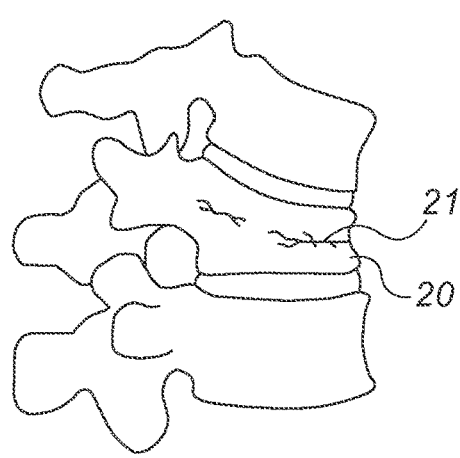
FIGS. 2A to 2D illustrate schematically the performance of a kyphoplasty procedure, performed on a collapsed vertebral body.
Figure 2B:
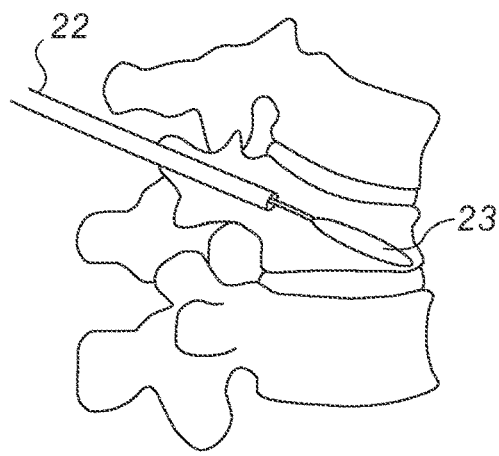
Figure 2C:
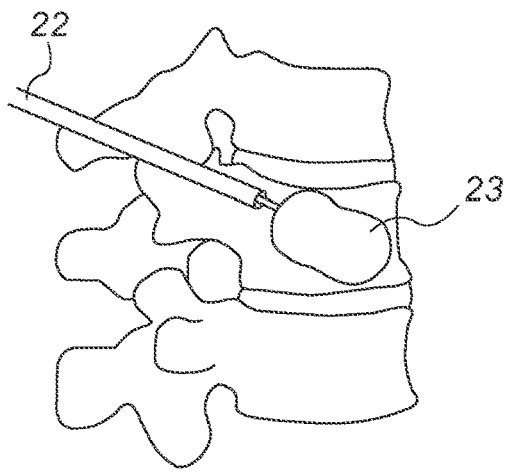
Figure 2D:
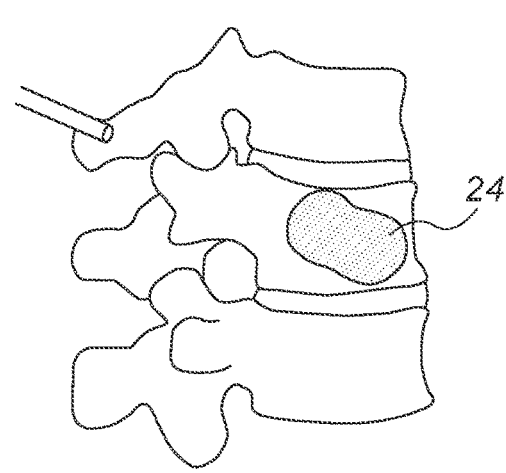

Reference is now made to FIGS. 2A to 2D, which illustrate schematically the performance of a kyphoplasty procedure, performed on a collapsed vertebral body 20. As is observed in FIG. 2A, as a result of fractures 21 in the vertebral body cortex, the relevant vertebra has suffered a partial collapse. In FIG. 2B, there is shown the insertion of a needle 22 through the pedicle region of the vertebra, with an inflation balloon 23 attached to its distal end. The balloon is inserted into the cancellous bone of the vertebra, or into a small void within the cancellous bone, as determined by preoperative imaging. In FIG. 2C, the balloon is shown being inflated, and in so doing, generating a large void within the body, and separating the vertebral end plates by the desired amount. Once the end plates have been separated sufficiently, the generated void is filled with bone cement 24, as shown in FIG. 2D, thereby supporting the distracted end plates, and relieving the vertebral collapse.

Figure 3:
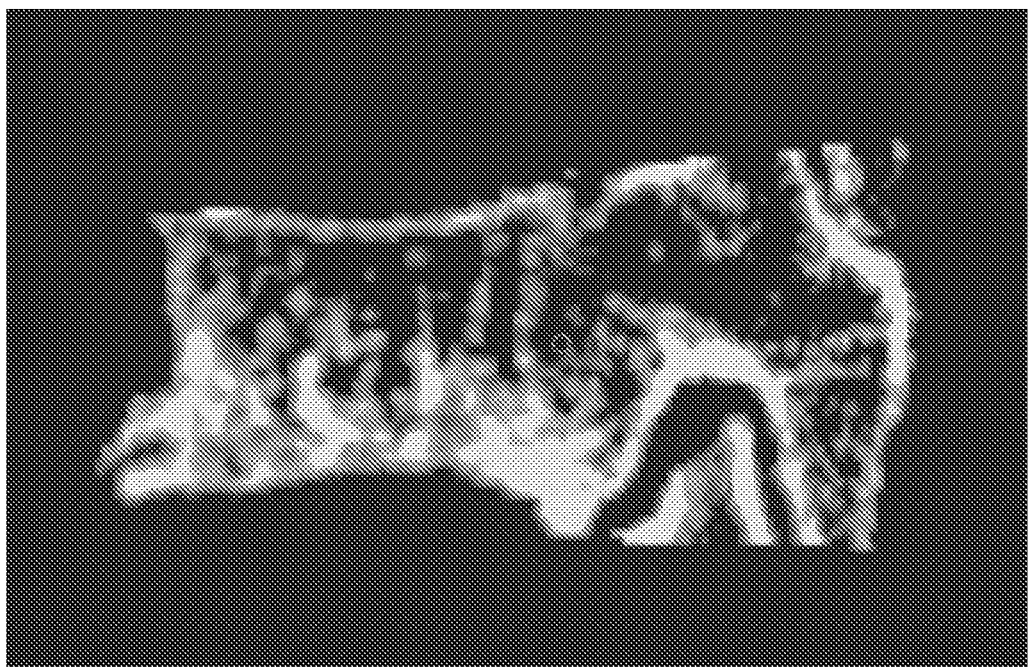
FIG. 3 is an image of a single CT slice of a lateral view scan of a vertebra before cement augmentation.

Reference is now made to FIG. 3, which is an image of a single CT slice of a lateral view scan of a vertebra before cement augmentation, showing the different absorption levels through the vertebral structure, as a result of different densities of bone through the vertebral structure. It is observed that the density of the bone throughout the vertebral body is not uniform, but that there exist passageways, niches and recesses of increased porosity bone, or even missing bone, into which the cement should be injected to ensure optimum filling. Some of those passageways lead externally out of the vertebral void, thus showing how leakage of the injected bone cement could occur.

Figure 4:
FIG. 4 is an image of stacked axial slices of a CT scan of a vertebra before cement augmentation.

Reference is now made to FIG. 4, which is an image of stacked axial slices of a CT scan of a vertebra before cement augmentation, showing the different absorption levels through the vertebral structure, as a result of different densities of bone through the vertebral structure.

Figure 5:
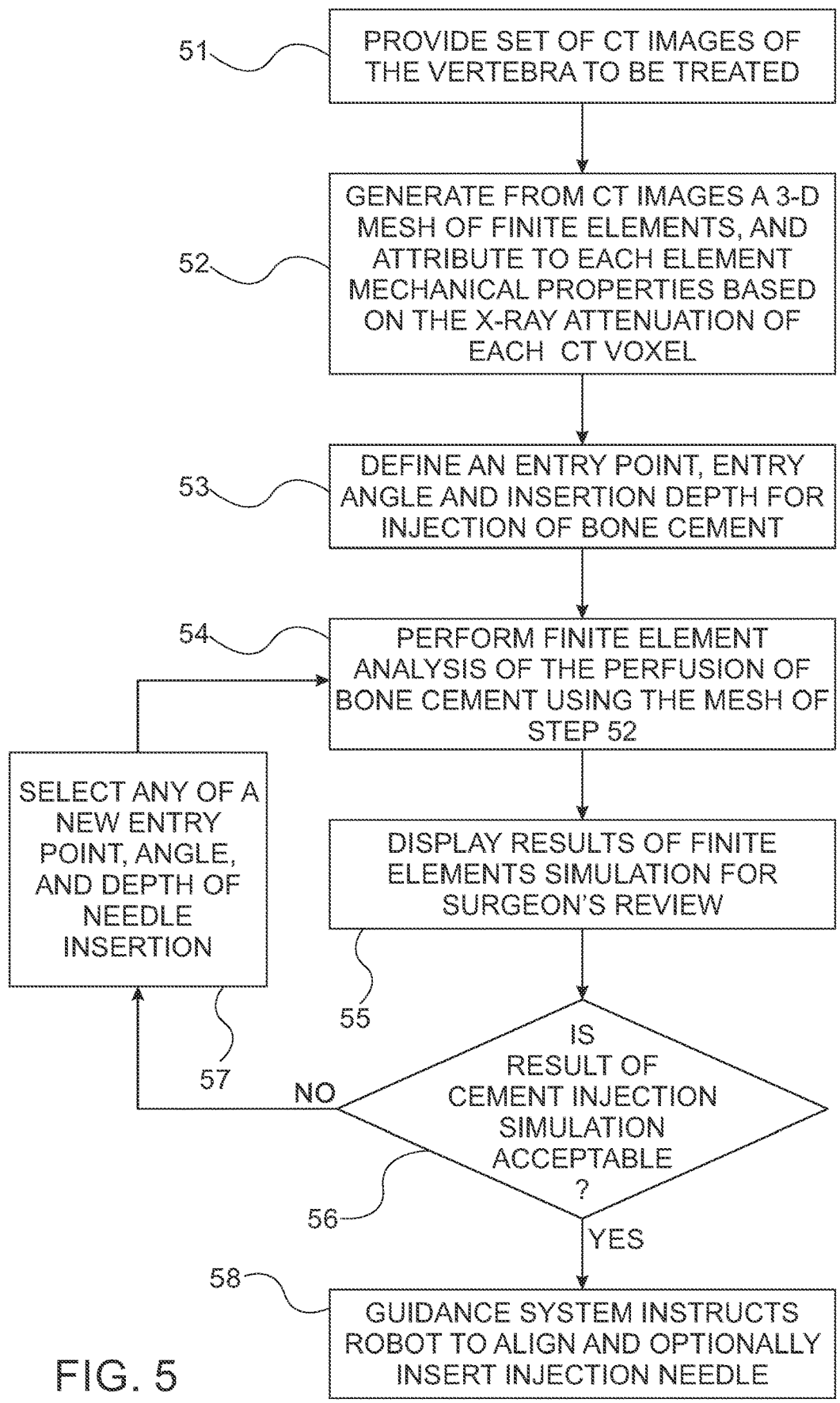
FIG. 5 is an example of a flowchart illustrating the steps required to execute one example of the methods of the present disclosure.

Reference is now made to FIG. 5 which is an example of a flowchart illustrating the steps required to execute one example of the methods of the present disclosure. The content of the flowchart has been described for a vertebroplasty procedure using a CT scan, and the steps of the invention can be as follows:

In step 51, a set of preoperative CT images of the vertebra to be treated is generated, showing the pathological features which the procedure is intended to correct.

In step 52, based on the shape and form of the preoperative CT scan, the volume of the vertebral body, and optionally of any surrounding parts of the vertebra, is transformed into a three dimensional mesh of Finite Elements. To each element of the mesh, there is then attributed mechanical properties of the bone, such as bone density, which may reflect its mechanical strength, or its porosity, the mechanical characteristics being based on the x-ray attenuation, generally expressed in Hounsfield Units (H.U.), of the corresponding voxel of the CT image. The entire 3-dimensional volume of the imaged vertebra is thus divided up into a three dimensional mesh, so that the spatial images of the attenuations can be transformed into that mesh, each voxel of the mesh showing the estimated equivalent mechanical characteristics of each voxel of the CT scan.

In step 53, the surgeon selects a point in the vertebral body through which he/she intends to inject the bone cement, and the spatial direction relative to a known axis, of a trajectory through that point, and up to the needle tip where the cement is to be ejected. In addition, the surgeon typically estimates a target amount of bone-cement to be inserted, based on a measurement on the 3-dimensional image set of the void to be filled in the vertebral body.

In step 54, a finite elements analysis is actuated on the mesh generated in step 52, and simulates the injection of bone-cement through the orthopedic void, from the tip of the planned trajectory at the point of the mesh previously selected in step 53, and in the direction of the orientation chosen. The calculation takes into consideration the mechanical properties, of the bone at every voxel within the vertebral body mesh, especially the bone porosity and the mechanical strength of the bone, the viscosity of the bone cement, which will determine the cement's flow characteristics through the entire mesh volume, the insertion pressure, and the amount of bone-cement injected.

In step 55, the result of the finite element analysis routine is displayed as a simulation of the deployment of the cement within the vertebral void, showing the final shape of the vertebra and the distribution of bone-cement obtained therein for that particular simulation.

In step 56, the surgeon, after reviewing the results of that simulation, determines whether the results are satisfactory, taking into account the bone cement propagation within the void of the vertebral body, whether there has been any leakage of cement or a shortfall of cement such that some spatial regions are still unsupported, and hence whether the initial parameters, such as the estimated amount of cement, were acceptable.

If the surgeon is dissatisfied with the outcome of the simulation, then in step 57, the surgeon can adjust the injection procedure, using any of more or less cement, selecting a different entry point or orientation angle, determining a different injection point, selecting a different cement composition, and selecting a different insertion pressure, in order to perform a further simulation, as executed by the return of the method algorithm to step 54. For example, if a simulation reveals that the cement leaks out of the vertebral body, a smaller quantity of cement may be selected. As another example, if the simulation reveals that the cement does not sufficiently fill the void, the quantity of cement can be increased accordingly. As yet another example, if the simulation reveals that all of the cement cannot deploy within the time allowed before viscosity of the cement becomes such as to prevent further significant flow, a cement composition having a reduced viscosity or a slower curing speed can be used. Once an acceptable simulation result has been obtained, the surgeon accepts the preferred entry point, the preferred trajectory, the preferred deployment point, and the amount of bone-cement to be introduced, and the insertion pressure for use in that procedure.

In step 58, the resulting parameters may be translated into instructions for transfer directly to a robotic guidance system, to mechanically guide the trajectory of the bone cement insertion device to the correct pre-selected and pre-planned location.

For a kyphoplasty procedure, the same steps are performed as for the vertebroplasty procedure of FIG. 5, with the addition of a step simulating the inflation of a balloon inside the vertebral body between steps 53 and 54. In general, the same insertion puncture will be used for balloon insertion and inflation and for cement insertion. The balloon position is set by the tip of the planned trajectory and in the direction of its alignment angle. The finite elements software can be adapted to include the effect of the balloon inflation on the mechanical properties of the vertebral body, simulating the inflation of the kyphoplasty balloon to the selected pressure and size, and the effects of application of the induced pressure on the finite elements in the mesh. The planning software can then continue with the routine described above, displaying the simulation and calculated results. Simulation of the injection of the bone-cement ensues.

Reference is now made to FIGS. 6A and 6B, which illustrate the generation of the finite elements mesh of the vertebral body. FIG. 6A shows a representation of the bone structure of the vertebral body, showing some bone porosity even on the outer cortical layer of the body. FIG. 6B shows an exemplary mesh constructed for the vertebral body, based on the absorption levels of the bone in the representation of FIG. 6A. The mesh in FIG. 6B is only visible on the vertebral surface, but it is understood to be a three dimensional mesh covering the entire volume of the body. To each individual mesh element there is attributed the corresponding mechanical property of the element as ascertained by the transformation of the H.U value of each element.

Reference is now made to FIG. 7 illustrates a finite elements mesh of a vertebra body, after a simulation of the injection of bone cement, the simulation being performed by means of a finite elements analysis, showing a concentration of the cement in the central region of the body. Such a display is of the type that would be used by the surgeon in step 56 of the method of FIG. 5, to ascertain whether the simulation of the cement augmentation resulted in an acceptable outcome.

Figure 8A:
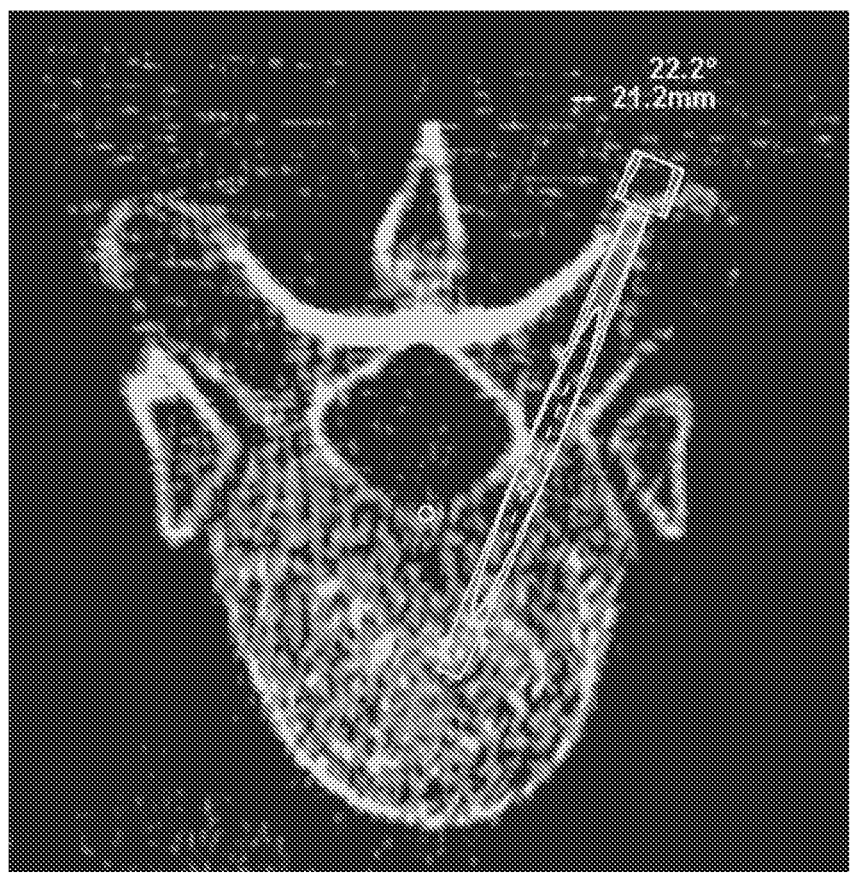
FIGS. 8A and 8B show the use of the selected needle trajectory, including the entry point, the orientation, and the ejection point, as determined by the method of FIG. 5.
Figure 8B:
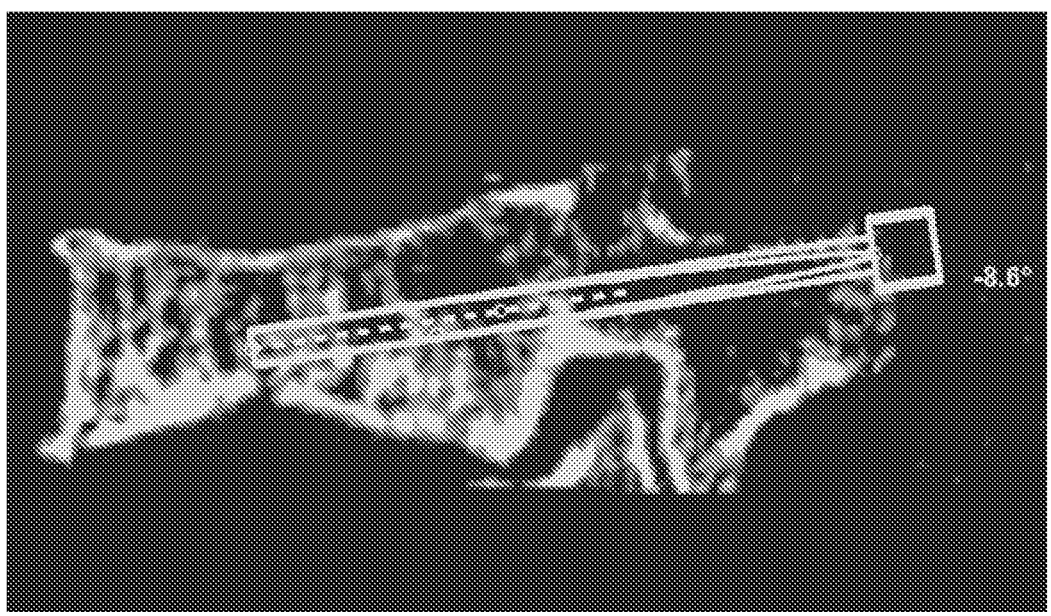

Reference is now made to FIGS. 8A and 8B, which show the use of the selected needle trajectory, including the entry point, the orientation, and the ejection point, as determined in step 56 of the method of FIG. 5, for the execution of the cement augmentation procedure by means of a robotic guidance system, as indicated in step 58 of the method of FIG. 5.

FIG. 8A shows an axial slice of a CT image of the vertebral body, with the insertion needle implanted on the image, as determined in the method of FIG. 5. On the image, there is shown the preferred insertion depth, with the entry point into the bone being 21.2 mm from the AP axis of the vertebra, and the selected angle being 22.2° from the AP axis of the vertebra.

FIG. 8B shows a lateral view of the same vertebral body, showing the tilt angle, −8.6°, of the insertion needle from the axial plane. These values can be input to the robotic control system, typically via the pre-operative planning software, that will in turn instruct the robot to align the surgical tools along the planned trajectory, for inserting the injection needle accurately at the desired pose and to the desired depth.

Figure 9:
FIG. 9 shows a view of stacked axial slices of a CT scan of a vertebra after cement augmentation.

FIG. 9 shows a view of stacked axial slices of a CT scan of a vertebra after cement augmentation. The accumulation of cement having a higher X ray attenuation than the remainder of the vertebral body, can be seen as the white region on the right hand side of the imaged body.

It is appreciated by persons skilled in the art that the present invention is not limited by what has been particularly shown and described hereinabove. Rather the scope of the present invention includes both combinations and subcombinations of various features described hereinabove as well as variations and modifications thereto which would occur to a person of skill in the art upon reading the above description and which are not in the prior art.

I claim:

1. A method of planning the insertion of bone cement into an orthopedic void of a vertebra, said method comprising:
generating from a three dimensional preoperative image comprising at least part of the vertebra, a three dimensional mesh of finite elements of said vertebra, each finite element representing a voxel or group of voxels of said three preoperative dimensional image;
using a predetermined conversion criterion, transforming image grey levels of said voxels into a spatial structure and/or a mechanical property of corresponding voxels of said vertebra, and attributing to elements of said three dimensional mesh of finite elements, said spatial structure and/or the mechanical property of said corresponding voxels of said vertebra, such that a three dimensional mesh of the spatial structure and/or the mechanical property of said at least part of said vertebra is generated;
selecting (i) a quantity of said bone cement, (ii) an entry point on said vertebra and (iii) an entry angle on said vertebra, through which to inject said bone cement into said orthopedic void;
using the known viscosity of said bone cement, and using said quantity of said bone cement and said entry point and entry angle, performing a finite elements analysis on said three dimensional mesh of the spatial structure and/or the mechanical property, to simulate the propagation of said bone cement into said orthopedic void; and
if said propagation is deemed unsatisfactory, repeating said simulation using at least one of a different quantity of bone cement, a cement of different viscosity, a different entry point, a different entry angle, a different cement delivery point, and a different cement insertion pressure,
wherein said propagation is deemed unsatisfactory if (i) said bone cement is shown to leak out of said vertebra, or (ii) said cement does not sufficiently fill said orthopedic void, or (iii) said bone cement does not deploy throughout said orthopedic void before the increased viscosity of said bone cement prevents its required further flow.

2. A method according to claim 1, wherein said repeating is performed iteratively until said propagation of said bone cement is deemed satisfactory.

3. A method according to claim 1, wherein said mechanical property is at least one of (i) bone porosity, (ii) bone density, (iii) Young's modulus, (iv) strain rate, (v) shear rate, and (vi) compressive strength.

4. A method according to claim 1, further comprising using the selected entry point and entry angle to provide information for input to a robotic guidance system for alignment of an injection device.

5. A method according to claim 1, wherein any of said simulations takes into consideration the increase in viscosity of said bone cement that is expected with the passage of time.

6. A method according to claim 1, wherein said three dimensional preoperative image is generated from a set of two dimensional images, or is obtained from a Computer Tomography (CT) scan.

7. A method according to claim 1, wherein said image grey levels correspond to x-ray attenuation levels.

8. A method according to claim 1, wherein said at least one of the different quantity of bone cement, the different entry point, the different entry angle, the different insertion pressure, the different cement delivery point and the cement of different viscosity, are determined by at least one of (i) a medical professional and (ii) a computerized program.

9. A method according to claim 1, wherein said at least part of said vertebra is the body of said vertebra.

10. A method according to claim 1, wherein said method obviates the need to fluoroscopically monitor said insertion of said bone cement.

11. A method of planning the insertion of bone cement into an orthopedic void of a vertebra;
generating from a three dimensional preoperative image comprising at least part of said vertebra, a three dimensional mesh of finite elements, each finite element representing at least on voxel of said three preoperative dimensional image;
using a predetermined conversion criterion, transforming image grey levels of said voxels into a spatial structure and/or a mechanical property of said voxels, and attributing to elements of said three dimensional mesh of finite elements, said spatial structure and/or the mechanical property of said voxels of said vertebra, such that a three dimensional mesh of the spatial structure and/or the mechanical property of a region of said vertebra is generated;
selecting (i) a quantity of said bone cement, and (ii) an entry point on said vertebra and (iii) an entry angle on said vertebra, through which to insert an inflation balloon into said vertebrae to generate an enlarged void, and through which to inject said bone cement into said void;
using said generated three dimensional mesh of the spatial structure and/or the mechanical properties of said vertebra, performing a finite elements analysis to determine a shape and extent of the enlarged void generated by inflation of said balloon;

using the known viscosity of said bone cement, and using said shape and extent of said enlarged void, performing a finite elements analysis on said three-dimensional mesh of the spatial structure and/or the mechanical property to simulate the propagation of bone cement injected into said enlarged void; and if said propagation is deemed unsatisfactory, repeating said simulation using at least one of a different balloon inflation condition, a different quantity of bone cement, a cement of different viscosity, a different entry point, a different entry angle, a different insertion pressure, and a different cement delivery point, wherein said propagation is deemed unsatisfactory if (i) said bone cement is shown to leak out of said vertebra, or (ii) said bone cement does not sufficiently fill said orthopedic void or (iii) said bone cement does not deploy throughout said orthopedic void before the increased viscosity of said bone cement prevents its required further flow.

12. A method according to claim 11, wherein said repeating is performed iteratively until said propagation of said cement is deemed satisfactory.

13. A method according to claim 11, wherein said mechanical property is at least one of (i) bone porosity, (ii) bone density, (iii) Young's modulus, (iv) strain rate, (v) Shear rate, and (vi) compressive strength.

14. A method according to claim 11, further comprising using the selected entry point and entry angle to provide information for input to a robotic guidance system for alignment of an injection device.

15. A method according to claim 11, wherein said simulation takes into consideration the increase in viscosity of said bone cement that is expected with the passage time.

16. A method according to claim 11, wherein said three dimensional preoperative image is generated from a set of two dimensional images, or is obtained from a Computer Tomography (CT) scan.

17. A method according to claim 11, wherein said image grey levels correspond to X-ray attenuation levels.

18. A method according to claim 11, wherein said at least one of the different balloon inflation condition, the different quantity of bone cement, the cement of different viscosity, the different entry point, the different entry angle, the different insertion pressure, and the different cement delivery point, are determined by at least one of (i) a medical professional and (ii) a computerized routine.

19. A method according to claim 11, further comprising selecting an insertion pressure at which to inject said bone cement into said void, and if said propagation is deemed unsatisfactory, repeating said simulation using a different insertion pressure.

20. A method according to claim 11, wherein said at least part of said vertebra is the body of said vertebra.

21. A method according to claim 11, wherein said method obviates the need to fluoroscopically monitor said insertion of said bone cement.

* * * * *